US010741042B2

(12) United States Patent
Devdas et al.

(10) Patent No.: US 10,741,042 B2
(45) Date of Patent: Aug. 11, 2020

(54) METHOD FOR TRACKING AND REACTING TO EVENTS IN AN ASSISTED LIVING FACILITY

(71) Applicant: PHILIPS NORTH AMERICA LLC, Andover, MA (US)

(72) Inventors: Vikram Devdas, Vancouver (CA); Shane McNamara, Vancouver (CA); Chris Pang, Vancouver (CA)

(73) Assignee: PHILIPS NORTH AMERICA LLC, Andover, MA (US)

( * ) Notice: Subject to any disclaimer, the term of this patent is extended or adjusted under 35 U.S.C. 154(b) by 0 days.

(21) Appl. No.: 16/236,254

(22) Filed: Dec. 28, 2018

(65) Prior Publication Data

US 2019/0236923 A1  Aug. 1, 2019

Related U.S. Application Data

(60) Provisional application No. 62/612,354, filed on Dec. 30, 2017, provisional application No. 62/735,837, filed on Oct. 31, 2018.

(51) Int. Cl.
*G08B 21/02* (2006.01)
*A61B 5/00* (2006.01)
(Continued)

(52) U.S. Cl.
CPC ............ *G08B 21/0227* (2013.01); *A61B 5/11* (2013.01); *A61B 5/1113* (2013.01); *A61B 5/1117* (2013.01); *A61B 5/1118* (2013.01); *A61B 5/16* (2013.01); *A61B 5/4809* (2013.01); *A61B 5/6802* (2013.01); *A61B 5/7275* (2013.01); *A61B 5/7282* (2013.01); *G08B 21/0423* (2013.01); *G16H 10/60* (2018.01); *G16H 40/00* (2018.01); *A61B 5/1123* (2013.01); *A61B 2562/0219* (2013.01); *G08B 21/0261* (2013.01); *G08B 21/0269* (2013.01); *G08B 21/0272* (2013.01)

(58) Field of Classification Search
CPC .. G08B 21/0227; A61B 5/1113; A61B 5/1118
USPC ................... 340/539.13, 539.1, 573.1, 572.1
See application file for complete search history.

(56) References Cited

U.S. PATENT DOCUMENTS

2005/0234310 A1\* 10/2005 Alwan ................. A61B 5/0002
                                                                600/300
2008/0001735 A1\* 1/2008 Tran ........................ A61B 7/00
                                                                340/539.22

(Continued)

*Primary Examiner* — Emily C Terrell

(57) ABSTRACT

A method for assessing health risk of a resident at a facility includes: tracking a first series of locations of a first wearable device associated with a resident of the facility; and tracking a first series of activities detected by the first wearable device; calculating a baseline action profile of the resident based on the first series of locations and the first series of activities; tracking a second series of locations of the first wearable device; tracking a second series of activities detected by the first wearable device; calculating a second action profile of the resident based on the second series of locations and the second series of activities; and in response to a deviation between the baseline action profile and the second action profile exceeding a deviation threshold, transmitting a prompt to a care provider associated with the facility to investigate a health status of the resident.

20 Claims, 5 Drawing Sheets

(51) Int. Cl.
*A61B 5/11* (2006.01)
*A61B 5/16* (2006.01)
*G16H 40/00* (2018.01)
*G16H 10/60* (2018.01)
*G08B 21/04* (2006.01)

(56) References Cited

U.S. PATENT DOCUMENTS

| | | | | |
|---|---|---|---|---|
| 2008/0015903 | A1* | 1/2008 | Rodgers | G06Q 30/02 |
| | | | | 705/3 |
| 2009/0002152 | A1* | 1/2009 | Chung | G08B 21/04 |
| | | | | 340/539.11 |
| 2011/0022189 | A1* | 1/2011 | Perry | H05B 47/105 |
| | | | | 700/12 |
| 2011/0291827 | A1* | 12/2011 | Baldocchi | G08B 21/043 |
| | | | | 340/539.11 |
| 2017/0005958 | A1* | 1/2017 | Frenkel | H04W 4/90 |
| 2017/0323155 | A1* | 11/2017 | Biswas | G01S 15/86 |

\* cited by examiner

METHOD FOR TRACKING AND REACTING TO EVENTS IN AN ASSISTED LIVING FACILITY

CROSS-REFERENCE TO RELATED APPLICATIONS

This Application claims the benefit of U.S. Provisional Application No. 62/612,354, filed on 30 Dec. 2017, and U.S. Patent Provisional Application No. 62/753,837, filed on 31 Oct. 2018, both of which are incorporated in their entireties by this reference.

This Application is related to U.S. patent application Ser. No. 15/339,771, filed on 31 Oct. 2016, which is incorporated in its entirety by this reference.

TECHNICAL FIELD

This invention relates generally to the field of senior and disabled care and more specifically to a new and useful method for tracking and reacting to the location of falls and other risk-laden events performed by a resident within an assisted-living facility in the field of indoor location services.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. First Method

Figure 1:
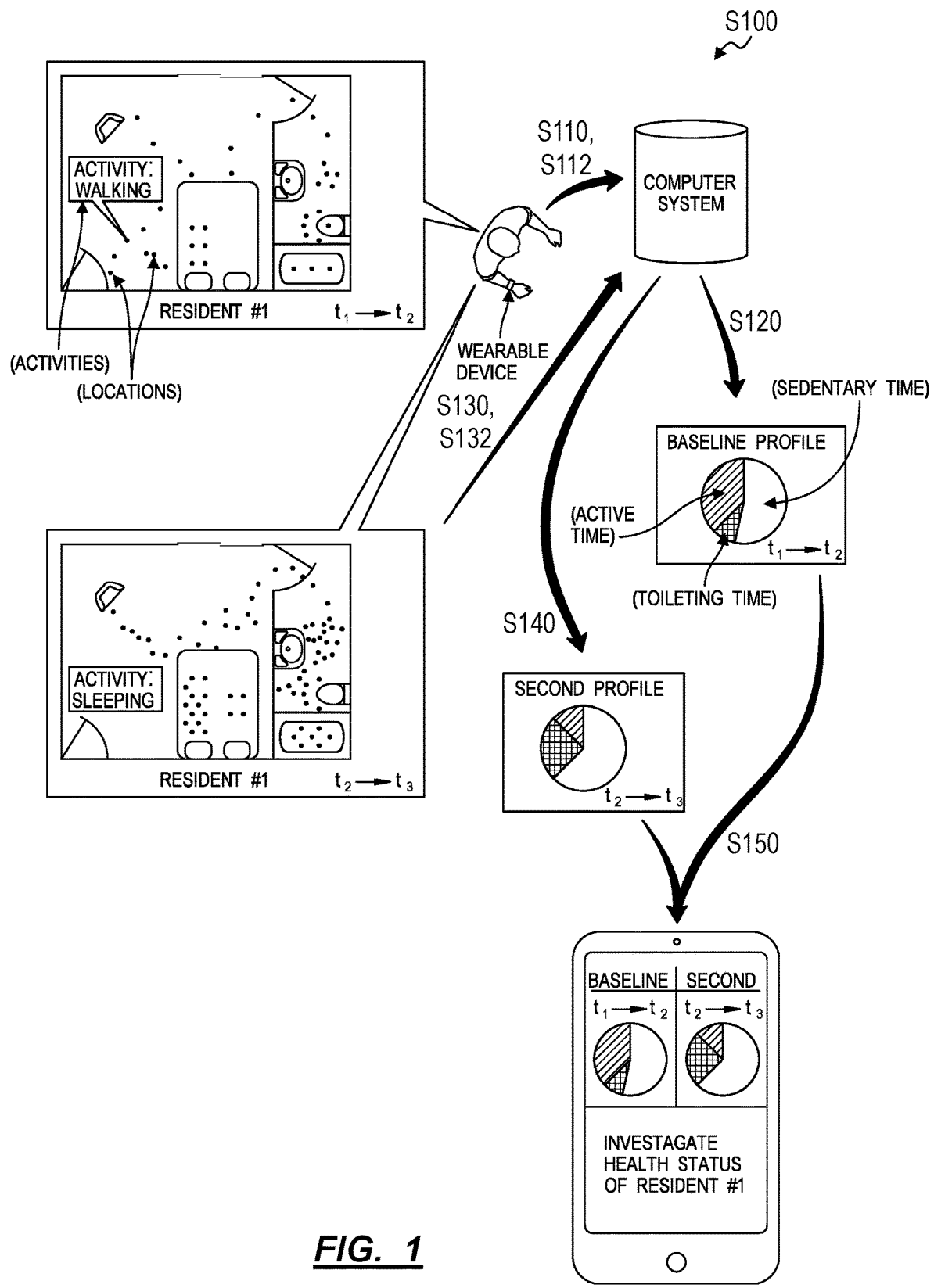
FIG. 1 is a flowchart representation of a first method.

As shown in FIG. 1, a first method S100 for assessing health risk of a resident at a facility includes, over a first period: tracking a first series of locations of a first wearable device associated with a resident of the facility in Block S110; and tracking a first series of activities detected by the first wearable device in Block S112. The first method S100 also includes: calculating a baseline action profile of the resident based on the first series of locations and the first series of activities in Block S120. The first method S100 further includes, over a second period: tracking a second series of locations of the first wearable device in Block S130; and tracking a second series of activities detected by the first wearable device in Block S132. The first method S100 also includes: calculating a second action profile of the resident based on the second series of locations and the second series of activities in Block S140; and in response to a deviation between the baseline action profile and the second action profile exceeding a deviation threshold, transmitting a prompt to a care provider associated with the facility to investigate a health status of the resident in Block S150.

Figure 2:
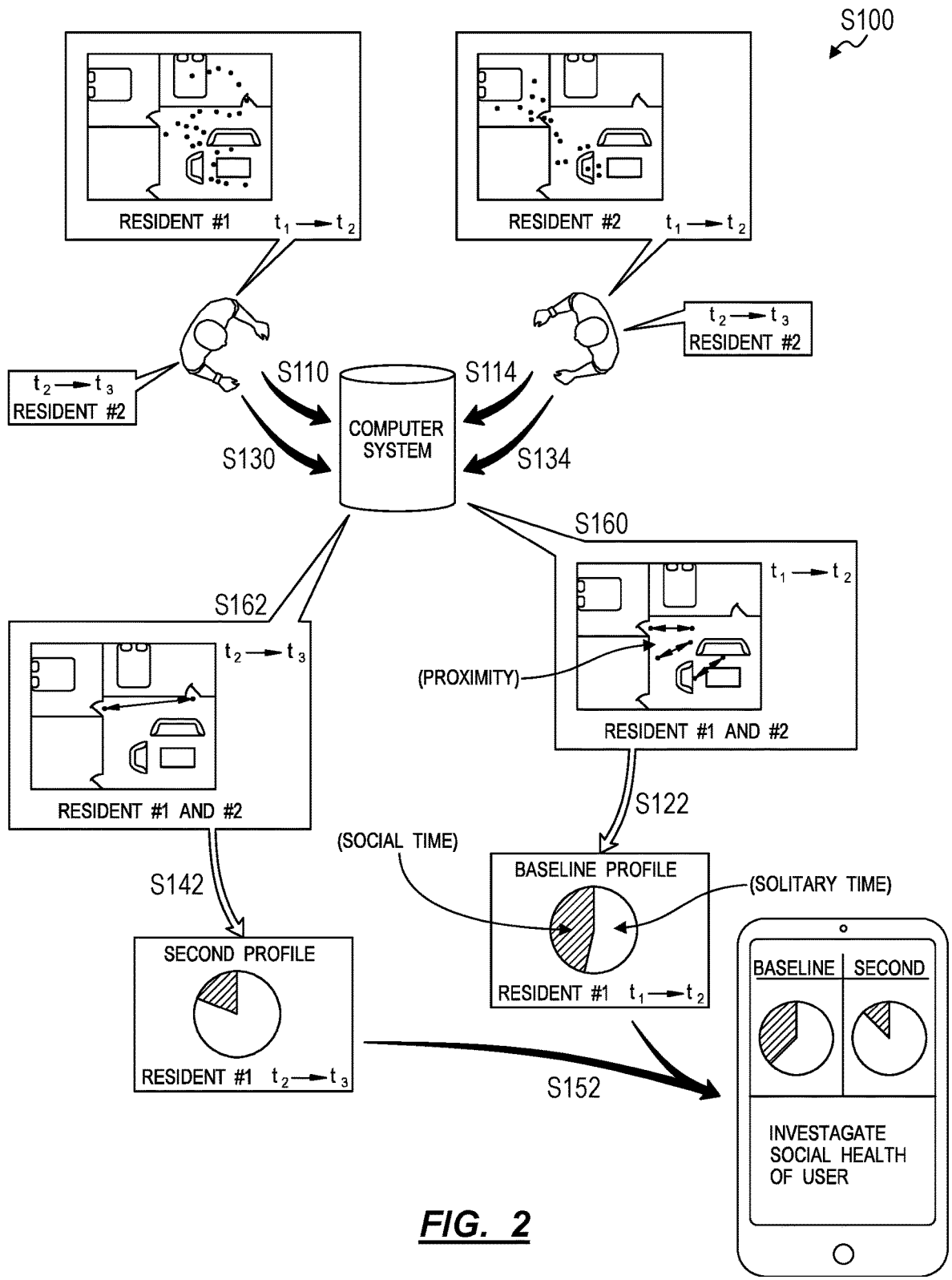
FIG. 2 is a flowchart representation of a variation of the first method

As shown in FIG. 2, one variation of the first method S100 for assessing health status of residents of a facility includes, over a first period: tracking a first series of locations of a first wearable device associated with a resident of the facility in Block S110; and tracking a second series of locations of a second device associated with a second user in the facility in Block S114. The variation also includes: calculating a first series of proximities of the first wearable device to the second device over the first period based on the first series of locations and the second series of locations in Block S160; and calculating a baseline interaction between the resident and the second user based on the first series of proximities in Block S122. The variation further includes, over a second period: tracking a third series of locations of the first wearable device in Block S130; and tracking a fourth series of locations of the second device in Block S134. The variation also includes: calculating a second series of proximities of the first wearable device to the second device over the second period based on the third series of locations and the fourth series of locations in Block S162; calculating a second interaction between the resident and the second user based on the second series of proximities in Block S142; and, in response to a deviation between the baseline interaction and the second interaction exceeding a deviation threshold, transmitting a prompt to a third user associated with the facility to investigate a health status of the resident in Block S152.

2. Second Method

Figure 3:
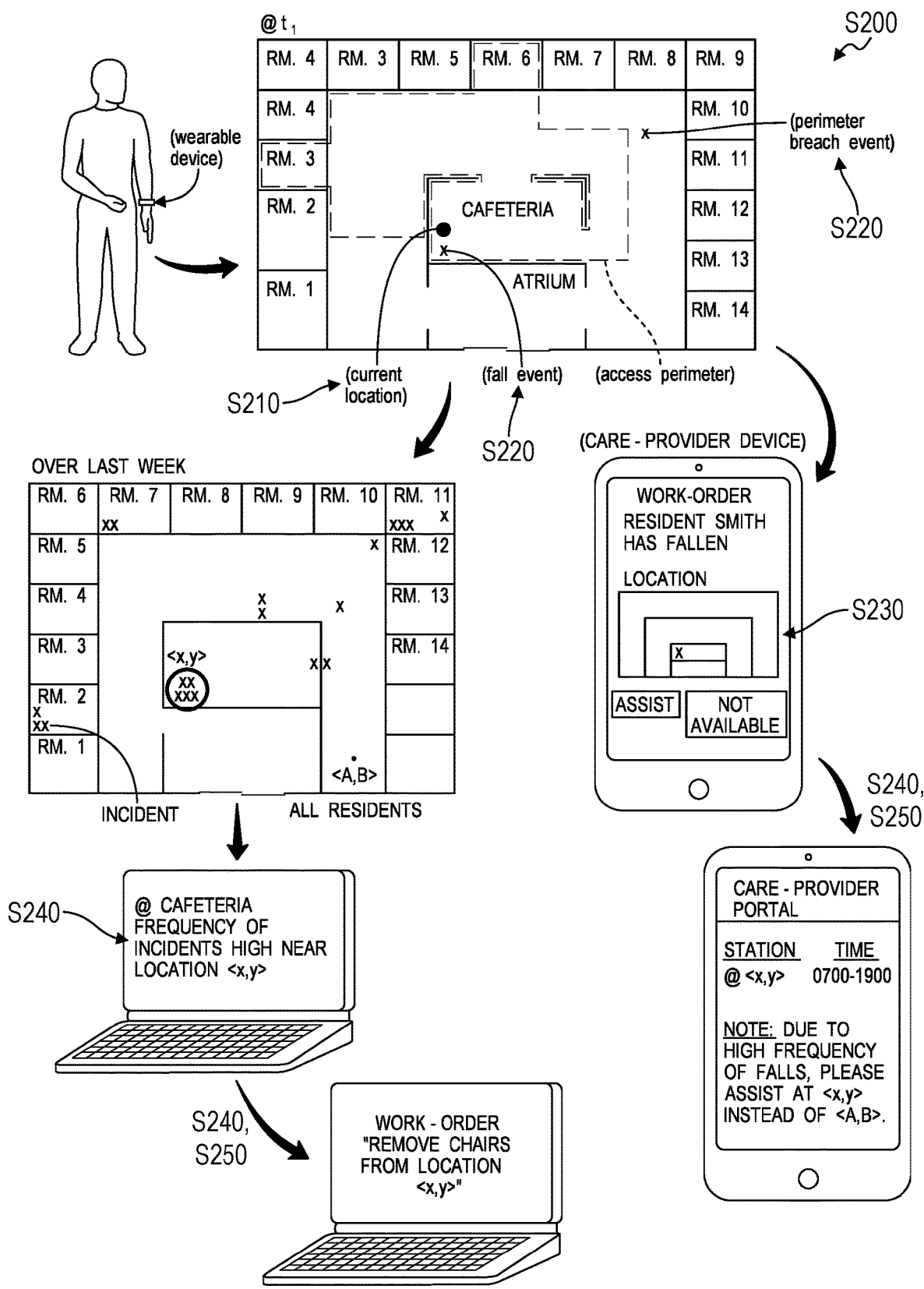
FIG. 3 is a flowchart representation of a second method.

As shown in FIG. 3, a second method S200 for tracking and reacting to events in an assisted-living facility includes: tracking a location of a first resident wearable device associated with a first resident of the assisted-living facility in Block S210. At the first resident wearable device: detecting a first incident by the resident proximal a first location of the assisted-living facility in Block S220; distributing the first location, time of the first incident, and details of the first incident to a set of computing devices associated with care providers affiliated with the assisted-living facility in Block S230; and, in response to frequency of incidents proximal the first location exceeding a threshold frequency during a time window, populating a work-order to deploy a care provider to the first location during the time window in Block S240; and distributing the work-order to the set of computing devices in Block S250.

One variation of the second method S200 includes: tracking a location of a first resident wearable device associated with a first resident of the assisted-living facility; in response to frequency of incidents—occurring within a threshold offset of a first location of the assisted-living facility—exceeding a threshold frequency, populating a work-order to deploy a care provider to remove a physical obstacle proximal the first location; and distributing the work-order to the set of computing devices.

Another variation of the second method S200 includes: tracking a location of a first resident wearable device associated with a first resident of the assisted-living facility; at the first resident wearable device, detecting a first incident by the resident proximal a first location of the assisted-living facility in Block S220; in response to frequency of incidents involving the first resident at the first location exceeding a threshold frequency, flagging the first location as a probable location for an incident; and, in response to detecting the resident approaching the first location, populating a work-order to deploy a care provider to the first location to assist the first resident; and distributing the work-order to the set of computing devices.

3. Applications: First Method

Generally, a set of wearable devices worn by a group of residents, a network of wireless hubs, and a computer system (hereinafter a "system") can cooperate to execute the Blocks of the first method S100 to: track locations of each individual resident throughout the assisted-living facility over time; detect activity of the resident (e.g., walking, sleeping, eating, etc.); detect intervention events for the resident (e.g., fall events, perimeter breach events, etc.); extract trends in the locations and mobilities of these residents to determine an action profile describing the typical activities of daily living (hereinafter "ADL") for each resident of the assisted-living facility; and detect and respond to changes in a particular resident's action profile, which may indicate improvement and/or worsening of the particular resident's physical or mental state.

The system can gather multiple types of data pertaining to a resident, in order to detect changes in the health (e.g., physical or mental) status of residents in the facility, including: a series of locations of the wearable device associated with the resident; a series of activities detected at the wearable device; and a series of intervention events detected at the wearable device. The system can also timestamp each of the series of locations, the series of activities, and the series of intervention events. Additionally or alternatively, the system can access electronic health records and/or demographic data of the resident to provide additional context for the behavior of the resident within the facility. The system can then utilize these sources of data to classify the action(s) being performed by the resident at any given time. After classifying the actions of the resident over an initial time period, the system can establish a baseline action profile for the resident. Subsequently, the system can calculate additional action profiles for the resident for comparison to the baseline action profile of the resident and, upon detecting deviations between a subsequent action profile and the baseline action profile, the system can transmit a prompt to investigate the health status of the resident.

The system can leverage location finding technology, such as ultrawideband (hereinafter "UWB") technology to estimate the location of a wearable device associated with a resident or care provider to within ten to twenty centimeters. With this level of accuracy, the system can associate extracted location and mobility trends of the resident with likely actions of the resident at corresponding times, such as: sleeping; grooming; toileting; in-room mobility; out-of-room mobility; and/or socialization; etc. Furthermore, the system can correlate contemporaneous activities detected by the resident's wearable device with the resident's concurrent location to confirm or further classify these actions of the resident.

The system can then calculate the amount of time a resident spends performing these actions to establish a baseline action profile for the patient. The system can periodically calculate a resident's action profile and compare this new action profile with the resident's baseline action profile in order to detect deviations unique to the resident over time. For example, if the system detects a deviation greater than a predetermined threshold between the new action profile and the baseline action profile, the system can output a notification to a native care provider application—executing on the care provider's computing device—indicating the status of the resident and the identified deviation to the resident's action profile, such as in real-time. In this example, the system can implement the deviation threshold as a conditional model indicating separate thresholds (e.g., proportional or absolute thresholds) for various actions identified in the action profile. Alternatively, the system can implement a risk assessment model that utilizes a machine learning approach to calculate a health risk assessment based on a difference between an updated action profile and a baseline action profile of a resident.

In addition to individual actions, the system can merge data from multiple residents and/or care providers to detect social or communal action (e.g., social eating, general social interaction, care provider time, etc.) amongst residents in the facility and between residents and care providers in the facility. The system can calculate proximity between two users in the facility by comparing the location data of each user and detecting when the two users are within a threshold proximity. Thus, the system can include individual interaction metrics (between a pair of users in the facility) and between a resident and all other members of the residential community. For example, the system can detect a total social interaction time for a resident, which can include interaction with both other residents or care providers in the facility. Additionally or alternatively, the system can detect interactions between a first resident and a second resident. In another example, the system can calculate a total amount of care time a resident has received in order to calculate insurance reimbursement payments. Thus, the system can detect changes in social behavior on a pairwise or wholistic basis for a resident and trigger prompts indicating a deviation from the resident's baseline level of social interactions.

In one implementation, the system can also modify the baseline action profile according to the requests of a physician in order to monitor compliance with the physician requests. For example, if a physician prescribes thirty minutes of exercise a day for a resident, the system can set a baseline of the "exercise" action in the resident's action profile at thirty minutes, such that the system can detect deviations from the prescribed amount of exercise time and alert care providers at the facility of the deviation.

4. Applications: Second Method

Furthermore, the system can execute Blocks of the second method S200 to calculate a frequency of incidents (e.g., falls, geospatial boundary breaches, and/or calls for assistance) within an assisted-living facility (hereinafter "the facility"), such as a retirement or nursing home. Based on the frequency of such events, the system can generate and transmit work-orders or other prompts to care providers and other staff in the facility to fix infrastructure issues near locations of common events and/or to allocate resources (e.g., care provider attention) to locations of high incident frequency in order to preempt further incidents at these locations. For example, the system can dynamically allocate care-givers in the facility to highly-trafficked areas where probability of incidents (e.g., fall events) is relatively high in light of historical georeferenced resident event data. In particular, the system can interface with wearable devices assigned to residents of the facility to detect instances in which residents of the facility fall, move beyond generic or custom access perimeters throughout the facility (hereinafter "perimeter breach events"), or request assistance through a call-button or other communication module. The system can respond to these incidents by transmitting prompts and event details to care providers within the facility substantially in real-time, thereby enabling care providers to rapidly seek and help residents involved in these incidents.

The system can track the location of each resident of the facility through their assigned wearable devices (e.g., at a rate of once per five-second interval or at a rate proportional to each resident's speed of motion through the facility). Motion sensors of the resident wearable device, such as an accelerometer and/or gyroscope sensor, can intermittently record motion data of the resident. In response to detecting motion data that aligns with (or is within a threshold offset of) a fall detection model, the system can detect and identify that the resident has fallen. Generally, in this implementation, the system functions to analyze motion sensor data to identify when a resident has fallen and to prompt care provider assistance for the resident at her location when a fall event is detected. Furthermore, the system can determine a location of the resident at the time of a fall event and serve prompts to care providers affiliated with the assisted-living facility—such as through their assigned mobile computing devices—to assist the resident at this location in Block S230.

Furthermore, the system can record incidents and locations of incidents within the facility over time and extract frequencies of incidents at particular locations throughout the facility from these data. In particular, the system can determine frequency of incidents for a single resident, a subset of residents within the residential community, or for all residents within the residential community. The system can then extract trends in these events and dynamically allocate resources (e.g., care providers, maintenance staff) according to these trends in order to reduce frequency and/or severity of future events. For example, in response to detecting a high frequency of fall events at a particular location within the facility, such as within a narrow boundary of radius less than a locational tolerance of resident-issued wearable devices, the system can: predict presence of a physical obstacle within the boundary; generate a work-order instructing a care provider or other staff of the facility to investigate and correct this physical obstacle that may be contributing to fall events at this particular location; and then selectively serve this work-order to employees of the facility. In this example, the system can identify six fall events and four calls for assistance near a communal bathroom in the facility over a period of one week. Due to a high frequency of incidents at this location, the system can populate a work-order to investigate fall events near the communal bathroom. The system can also merge incident data and this work-order with video (e.g., security) footage of this location to assist care providers in determining why residents stumble in this location (e.g., due to presence of a chair obscuring a direct path between the communal bathroom and a nearby cafeteria).

The system can similarly extract a relationship between fall events (or other incidents) with a location and density of residents present at this location and selectively serve prompts to care providers to monitor a particular location associated with a relatively high frequency of fall events when a group of residents is present. In particular, the system can dynamically allocate care providers to a particular location as a function of an historical rate of fall events at this location and the current (or predicted near-future) density of residents at this location.

Similarly, the system can track each resident of the assisted-living facility, detect locations of fall events in which each resident is involved, and, in response to detecting a high-frequency of fall events by a particular resident, such as at a particular location in the facility, preemptively deploy a care provider to assist the particular resident when occupying or approaching this particular location.

Therefore, the system can be configured to identify fall-prone residents within the facility and to selectively deploy a care provider to assist these fall-prone residents based on location, motion, and/or trajectories of these residents before a fall event. Thus, the system can execute Blocks of the second method S200 to: improve care provider reaction speed in response to an incident; decrease care provider idleness; improve care provider efficiency; reduce resident risk for incidents and injuries by preemptively stationing assistance in areas where residents are at greater risk for incidents; automatically detect early signs of physical and/or mental health changes for a resident and to selectively prompt additional assistance for this resident accordingly; etc. based on trends extracted from location data of residents in the facility.

5. System

A system—such as a local computer system within an assisted living facility (e.g., a local server), a remote server (e.g., "in the cloud"), or a distributed computer network, etc. (hereinafter "system"), can execute the methods S100 and/or S200. In particular, the system can interface with multiple devices (e.g., "beacons") within and around a facility in order to track positions of various residents and care providers within the facility. Furthermore, the methods S100 and S200 described herein are implemented within or in conjunction with an assisted-living facility. However, the methods S100 and S200 can be similarly implemented within a general hospital, a psychiatric hospital, a preschool, a summer camp, or any other health institution, clinic, or community. Similarly, the methods S100 and S200 are described below as implemented by a facility to serve a resident of the assisted-living facility, though the methods S100 and/or S200 can additionally or alternatively be implemented to serve a resident at a general hospital, a student at a school, or a child at a day care or summer camp, etc. The methods S100 and S200 can be similarly implemented by a facility to guide a care provider—such as a nurse, a teacher, or a camp counselor—to serve such residents or students and to, in real-time, update family members, friends, physicians, insurance providers, etc. of a resident's health and well-being.

In particular, Blocks S110-S162 of the first method S100 and Blocks S210-S250 of the second method S200 can be executed by a system, such as on a local system within an assisted living facility (e.g., a local server), by a remote server in the cloud, or by a distributed computer network (hereinafter "system"). In particular, the system can interface with multiple devices (e.g., wearable devices or mobile devices, such as a smartphone tablet, etc.) within and around the assisted living facility (the "facility") to handle and respond to proximity events for residents of the facility. Additionally or alternatively, Blocks of the methods S100 and S200 can be executed by a local or remote system that interfaces with a set of wearable devices assigned to a group of residents and to a group of care providers, one or more wireless communication hubs within or around an assisted living facility, and/or a set of computing devices assigned to the group of care providers.

In one implementation, an administrator of the facility can access an administrator interface to assign a resident of the facility one or more (i.e., a set of) wearable devices. For example, the administrator may assign two wearable devices to a resident, including: a first wearable device to be worn by the resident during the day and recharged at night; and a second wearable device to be worn by the resident at night and recharged during the day. Each resident wearable device can be loaded with a unique ID (e.g., a WIRELESS ID), and the unique ID can be associated with a particular resident of the facility, such as in a name mapping server (or "NMS"). In this implementation, the resident wearable device can include: a set of inertial sensors; a processor configured to classify its motion (e.g., sleeping, sitting, walking, running, and a rate of each) based on outputs of the inertial sensor(s); a geospatial location sensor (e.g., a GPS sensor or an UWB compatible transmitter); a wireless communication module that broadcasts location data; and/or a rechargeable or replaceable battery that powers the foregoing elements.

In the foregoing implementation, the administrator of the facility can assign or otherwise provide a care provider—employed by the facility—with one or more care provider wearable devices and/or computing devices. A care provider wearable device can be substantially similar to the resident wearable device, as described above. The care provider wearable device and the resident wearable device can additionally or alternatively include: a short-range wireless communication module (e.g., a low power 2.4 GHz wireless communication device); an inertial sensor (e.g., an accelerometer and/or gyroscope sensor); an input field (e.g., a touchscreen); a processor; and/or a rechargeable battery. The processor can detect proximity between the care provider wearable device and resident wearable device to confirm contact between the care provider and the resident based on outputs of the inertial sensor.

As shown in FIG. 3, a computing device (e.g., a tablet or a smartphone) assigned to a care provider can execute a native care provider application, as described below. Additionally or alternatively, an instance of the native care provider application can be installed on a private computing device owned by a care provider, such as the care provider's personal smartphone or tablet. For example, the native care provider application can: receive a work-order (or incident report or prompt) from a local or remote server which can alert a care provider of the incident through a user interface (e.g., on an integrated display); receive a response to the work-order (e.g., "No, I cannot respond right now") from the care provider through the interface; and upload the work-order responses to the remote server. Furthermore, the native care provider application can serve an incident report to the care provider through the interface; collect data entered into the incident report manually by the care provider; and communicate these data back to the server.

Additionally, the native care provider application can display prompts transmitted by the system corresponding to various incidents (e.g., fall events) detected by the system. For example, in Block S150, the system can, in response to a deviation between the baseline action profile and the second action profile exceeding a deviation threshold, transmit a prompt to a care provider associated with the facility to investigate a health status of the resident. In another example, in Block S152, the system can, in response to a deviation between the baseline interaction and the second interaction exceeding a deviation threshold, transmit a prompt to another user associated with the facility to investigate a health status of the resident. In these examples, the computing devices associated with the care provider can display the prompts transmitted by the system via the native care provider application. Furthermore, the native care provider application can provide interfaces and/or tools for scheduling physician appointments or additional care provider time for a resident.

Regarding the second method S200, the care provider application can populate and distribute work orders to address areas of the facility associated with a higher frequency of fall events. The native care provider application can display the work order distributed by the system and can display fields of the work order that the system can populate. Thus, a care provider or administrator using the native care provider application can edit the prepopulated fields of the work order after the native care provider application has displayed the work order.

However, the system can notify care providers and/or other users (e.g., administrators) of the facility of action profile deviations, interaction deviations, and/or work orders associated with intervention events in any other way.

6. Location Tracking

Blocks S110, S114, S130, and S134 of the first method S100 recite tracking a series of locations of a wearable device associated with a resident of the facility. Generally, in Blocks S110, S114, S130, and S134 of the first method S100, the system cooperates with the resident's wearable device, one or more local wireless communication hubs interspersed throughout the facility (e.g., mounted to walls of the facility), and/or any other device within proximity of the resident's wearable device to determine the location of a resident. In particular, the system can determine and track a location of each resident wearable device deployed throughout the facility in Blocks S110, S114, S130, and S134. Additionally, the system can track a location of each care provider wearable device deployed throughout the facility. For example, the system can track an absolute geospatial location of the resident within the facility or a location of the resident relative to one or more wireless communication hubs or other wireless-enabled devices of known location within the facility. Furthermore, the system can track the location of the resident with a greater degree of accuracy (e.g., to within twenty centimeters) by leveraging UWB technology. With greater location resolution, the system can more accurately estimate the various actions of a resident. Furthermore, the system can also leverage other wearable devices to track the location of a wearable device based on its proximity to another resident wearable device. For example, the wearable devices can detect proximity to each other by measuring the signal strength of a wireless transmission from another wearable device. In some implementations, the system can also detect the proximity between two wearable devices directly based on signal strength measurement.

Additionally, the system can track the location of wearable or other computational devices associated with residents and or care providers relative to the floorplan of the facility. In one implementation, the system can access a geofence in the floorplan associated with the resident that also corresponds to a location-based action of the resident; and calculate a baseline action profile of the resident including the location-based action based on the first subset of locations. Thus, the system can correlate the location of the resident at a given time with a particular action typically undertaken in that location of the floorplan. For example, if the system tracks a resident's location with a geofence corresponding to the location of a toilet in the floorplan, the system can determine that the resident is performing a "toileting" action and include the toileting action in the action profile of the resident.

The process for detecting each location in each series of locations is further described in U.S. patent application Ser. No. 15/339,771, which is herein incorporated in its entirety by this reference. The resident's wearable device can broadcast a test signal to one or more local wireless communication hubs of known location(s) within the facility. The resident wearable device can then receive return signals and wireless IDs from the wireless communication hub(s), calculate a flight time for the test signal, and transmit these wireless IDs and corresponding flight times of the test signals (via a local wireless hub) to the system, which can then reconstruct the location of the resident's wearable device—and the resident—from these data. For example, if a single wireless communication hub is within wireless range of the resident's wearable device, the system can determine that the resident is within a circular area centered at the known location of the wireless communication hub by: referencing the wireless ID received from the wireless communication hub to a map of the facility; and calculating the radius of the circular area based on the flight time of a test signal broadcast by the wearable device and then received from the wireless communication hub.

In the foregoing implementation, the resident wearable device can also: collect wireless IDs and test signal flight times from two or more local wireless communication hubs; and transmit these wireless IDs and test signal flight times to the system via a local wireless communication hub. The system can then implement similar techniques to determine the location of the resident within the facility, such as by locating (e.g., via multilateration) the position of the resident's wearable device within the facility relative to the three (or more) wireless communication hubs. The system can also locate the resident's wearable device based on proximity to other devices within the facility, such as based on flight times of test signals broadcast by the resident's wearable device and returned from other resident wearable devices, care provider wearable devices, and/or computing devices within the facility.

In the foregoing implementations, the system can determine the location (e.g., a point, an area) of the resident's wearable device based on time of flight data received from one or more wireless communication hubs and/or other wireless-enabled devices in communication with the resident's wearable device (e.g., a mobile computing device associated with the resident and communicatively coupled to the resident wearable device) regularly during operation. For example, the system can cooperate with the resident's wearable device to implement a static location tracking rate, such as once per minute or once per five-second interval. Alternatively, the system and resident wearable device can implement a dynamic location tracking rate. For example, a controller integrated into the resident wearable device can predict the user's current activity—such as sleeping, sitting, walking, or running, etc.—based on outputs of motion and/or inertial sensors integrated into the wearable device. When the resident is determined to be sleeping or sitting, the wearable device can broadcast a wireless signal—which may be collected by local wireless communication hubs and transformed into a location of the wearable device by the system—at a rate of once per five-minute interval. When the resident is determined to be walking slowly, the wearable device can broadcast a wireless signal at a rate of once per ten-second interval; as the resident's speed of motion increases, the wearable device can increase its broadcast rate, such as up to a maximum broadcast rate of once per five-second interval. Furthermore, in response to an incident, the system can transmit a command to increase the broadcast rate to 1 Hz to the wearable device (e.g., via a local wireless communication hub).

However, the resident's wearable device, the wireless communication hub(s), and/or the system can cooperate in any other way to determine the location of the resident's wearable device. The resident's wearable device, the wireless communication hub(s), and/or the system can repeat these processes over time to track the location of the resident throughout the facility. In particular, based on the resident's location, the system can generate a map (e.g., "heat map," a "breadcrumb trail") of the resident's locations within the facility to identify popular locations and/or routes of the resident. Thus, the system can extract various resident-specific data from this map, such as when and where the resident spends her time (or most of her time), the resident's physical activity level and mobility level, with whom the resident spends her time, and whether any of these metrics have changed, which may indicate a change in the resident's comfort level in the facility, friend group, physical health, and/or mental health.

As described below, the system can implement similar methods and techniques to track locations of other wearable devices assigned to and worn by other residents of the facility over the same period of time. In Block S210 of the second method S200, the system can implement similar methods and techniques to track locations of a wearable device associated with the resident of the facility.

7. Incidents: Single Resident

Blocks S220 and S230 of the second method S200 recite at the first resident wearable device: detecting a first incident by the resident proximal a first location of the assisted-living facility in Block S220 and distributing the first location, time of the first incident, and details of the first incident to a set of computing devices, each computing device in the set of computing devices associated with a care provider affiliated with the assisted-living facility in Block S230. Generally, the system can execute Blocks S220 and S230 of the second method S200 to record incidents (e.g., fall events, breaches of an access perimeter, and/or calls for assistance from a resident), residents involved in these incidents, and locations of these incidents. In particular, in response to detecting incidents, the system can merge incident data with locations of the resident in the facility to log various data representative of incidents involving the resident over time. For example, the system can generate an incident map through which a care provider, administrator, facility insurance provider, physician, and/or family member may view locations in which incidents involving the resident have frequently occurred.

Additionally, the system can track incidents for inclusion in an action profile of a resident. For example, the system can track a series of fall events detected by a wearable device; and calculate an action profile of the resident based on a series of locations, a series of activities, and the series of fall events. The system can track an incident frequency over a period of time, a number of incidents over a period of time, and/or a severity of incidents over a period of time.

7.1 Incident Location Detection

In one implementation, the system can calculate a frequency of incidents in which a particular resident is involved at a particular location, within a particular region, and/or within a particular room inside the facility over a period of time (e.g., one week, one month, one year, etc.). The system can discretize the facility into discrete areas (or regions) according to: a grid (e.g., with ten feet by ten feet discrete areas) distributed across the facility; rooms of the facility (e.g., a cafeteria is a first region, a resident's room is a second region, a communal bathroom is a third region); and/or frequency of incidents within a clustered area. For example, the system can extract a first area encompassing a three meter by three meter area near a corner of the cafeteria in response to detecting four falls by a particular resident within the first area over the past month; and a second area encompassing the remaining area of the six meter by six meter cafeteria in response to detecting four falls by the particular resident within the second area over the past month. In response to the frequency of incidents within a particular area exceeding a threshold frequency (e.g., four incidents per month), the system can then populate a work-order instructing care providers to assist the particular resident when the particular resident is coincident the particular area, as described below.

Additionally or alternatively, the system can calculate frequencies for each type of incident (e.g., falls, breaches, and calls for assistance). Thus, the system can determine which types of events are more likely (or less likely) at discrete locations within the facility. For example, the system can calculate for a resident: a frequency of falls within the resident's room as one fall per month; a frequency of breaches outside the resident's access perimeter (e.g., outside their room into a neighbor's room) as one breach per month; and a frequency of calls for assistance within the resident's room as eight times per month. The system can thus determine that the resident is cautious within her room and is inclined to request assistance prior to a fall or other injurious incident. Thus, the system can populate a work-order instructing care providers to be available to the resident when the resident requests assistance; however, the system can deploy care providers to other resident's rooms who may be more inclined to fall prior to calling for assistance (i.e., their frequency of falls exceeds their frequency of calls for assistance).

In another implementation, the system can calculate a frequency of incidents (of one type or multiple types) proximal a particular area of the facility or across the entire facility for discrete times of day. For example, a resident may fall more frequently during night hours (e.g., 10 pm to 5 am) and less frequently during day hours (e.g., 5 am to 7 pm). Thus, the system can identify when and where a resident may seek assistance and selectively deploy care providers to accompany (or assist) the resident during night hours to limit a number of falls during the night.

However, the system can calculate a frequency of incidents in any other suitable manner to determine and predict risk of discrete locations of the facility and times of day for each resident within the facility.

7.2 Incident-Triggered Outputs for Individual Resident

In response to detecting a high quantity (or frequency) of fall events by a particular resident, the system can populate a work-order to deploy a care provider to assist the particular resident globally or at particular times and/or particular locations within the assisted-living facility where the particular resident may be inclined to fall. In one implementation, the system can detect that the particular resident was involved with a disproportionately high frequency of fall events (as described below) in a first location of the facility relative to other residents. Thus, the system can populate the work-order to deploy a care provider to the first location when the particular resident is proximal the first location. Similarly, the system can detect that the particular resident exhibits a high frequency of fall events at a particular time of day and/or day of week. For example, a first resident may fall frequently after bingo on Wednesday nights. Thus, the system can populate a work-order to deploy a care provider to the first resident's location just prior to an end of bingo night on Wednesdays. Thus, as shown in FIG. 5, the system can prioritize residents who may exhibit limited mobility or another ailment which may contribute to high quantity of incidents, such as falls or calls for assistance.

Additionally or alternatively, the system can populate the work-order to include a list of residents involved with or proximal to locations of past incidents affiliated with a particular resident. For example, a first resident may fall more frequently when accompanied by her friends, a second resident and a third resident. The work-order can inform a care provider that the first resident may be more likely to fall when surrounded by the second and third resident and prompt the care provider to separate the first, second, and third resident.

Figure 4:
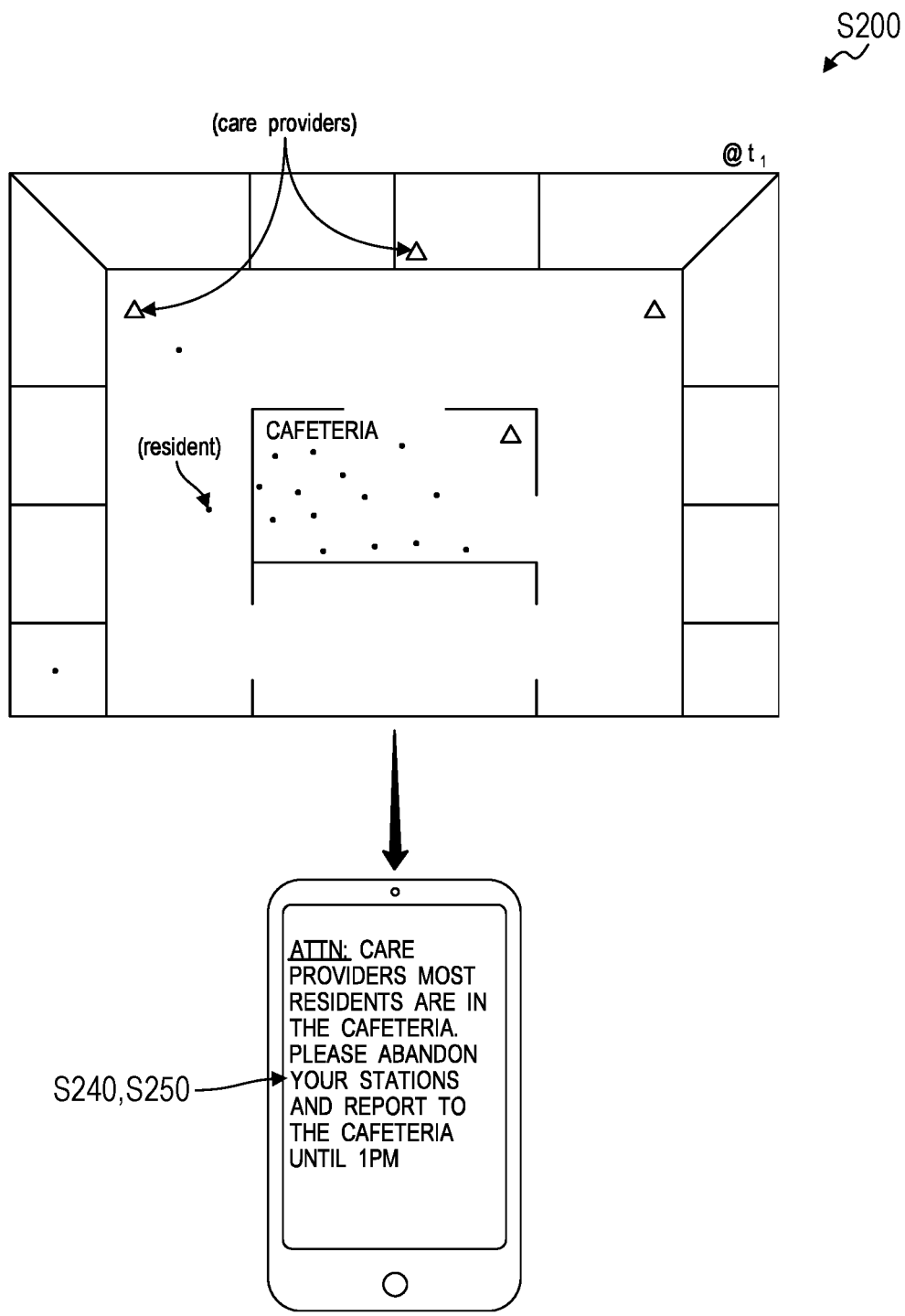
FIG. 4 is a flowchart representation of a variation of the second method.
Figure 5:
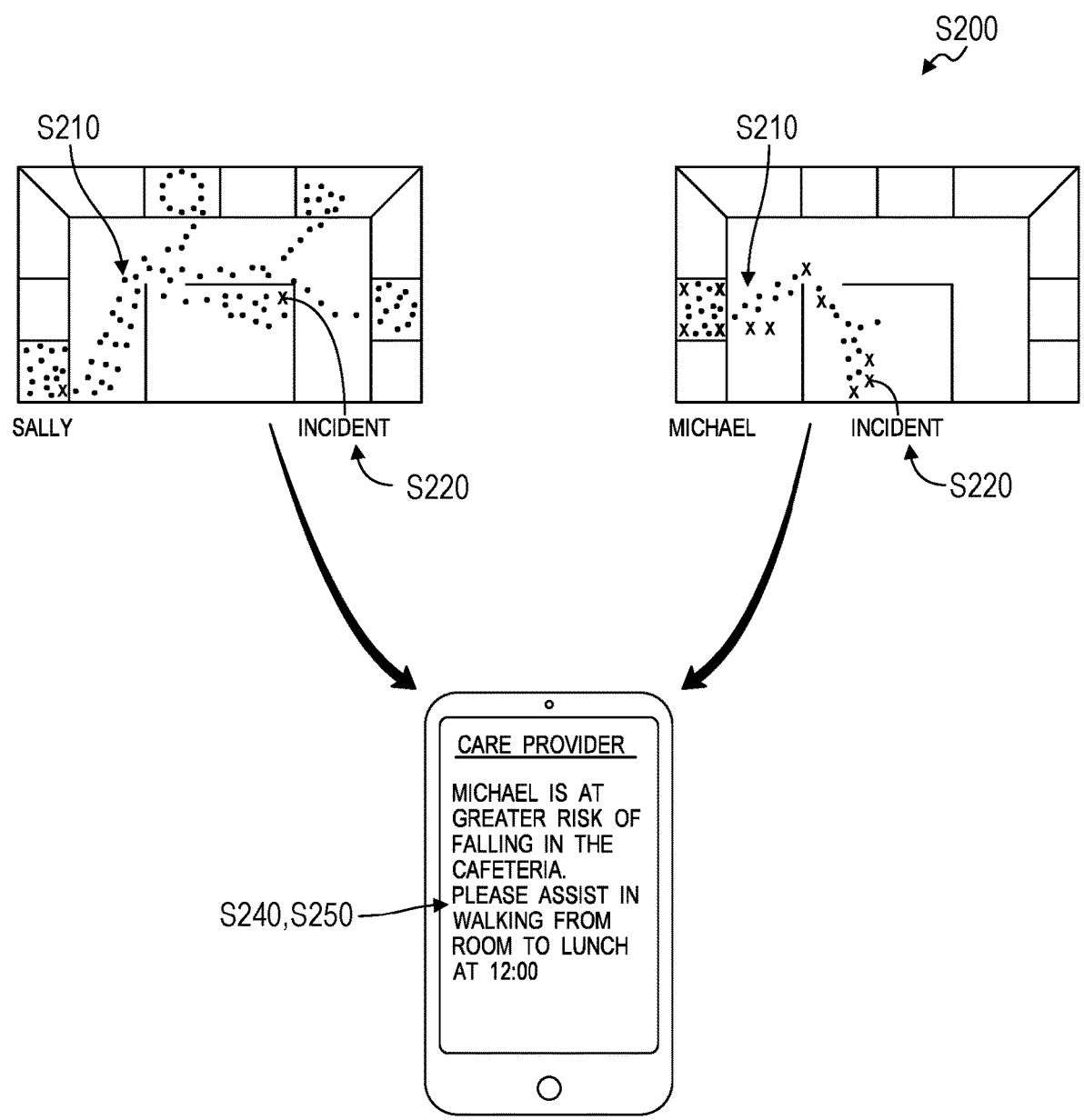
FIG. 5 is a flowchart representation of a variation of the second method.

In one variation shown in FIGS. 4 and 5, the system can also: generate maps for each resident (and/or all residents) within the facility; display these the care provider portal to inform the care provider of the current location of each resident and the past locations occupied by the resident (e.g., geospatial locations, regions, areas, room, etc. of the facility or surrounding areas); and predict locations occupied by the resident at future instances in time. Based on the map, the system can identify a particular resident with decreased mobility patterns (or downwardly-trending mobility patterns). Thus, in this variation, the system can identify variation in behaviors of each resident to efficiently identify when a particular resident may be depressed, may be less mobile, and when a particular resident is at higher risk for an incident based on changes in the resident's mobility over time.

For example, the system can determine—from location data collected over a period of two months—that a first resident visits rooms of a second resident and a third resident on a daily basis. However, the system can determine that the first resident has visited the second resident's room but not the third resident's room and that the resident has not met the third resident elsewhere in the facility during these past four days based on a map representing the first resident's locations during these past four days. Accordingly, the system can flag the change in the first resident's social behaviors and notify a care provider in the facility that the first resident may have had a disagreement with the third resident, may be experiencing increased depression or anxiety, may be ill, and/or may be experiencing decreased mobility and therefore not visiting the third resident's room. Therefore, as shown in FIG. 5, the system can prompt the care provider to monitor the first resident more closely or check-in with the first resident to determine if she requires additional medical attention. Additionally or alternatively, the system can prompt family members, friends, and/or other visitors to visit or check-in with the first resident.

In one variation, based on recorded incidents, the system can then project where the resident is likely to experience incidents in the future. For example, the system can identify a cluster of incidents in which a particular resident is involved proximal a particular location of the facility and flag the location as possibly hazardous for the particular resident. As described below, the system can then populate a work-order to deploy a care provider to the particular location to assist the resident prior to an incident or fix the particular location (e.g., arrange furniture to remove obstacles, fix a bump in carpet, etc.) to help the resident avoid incidents at the particular location in the future.

8. Incidents: Community

In one variation shown in FIG. 4, the system can merge data from multiple residents' wearable devices to generate a map of locations of residents (e.g., tracked across every hour of every day) and incidents of all residents within the facility. Generally, the system can, as described above, track incidents and locations of incidents for each resident within the facility and merge incident and location data to calculate a global frequency of incidents for all residents (or the subset of residents) within the facility. Thus, the system can identify problematic (i.e., high-risk) areas within the facility and either allocate resources to the problematic areas or implement a structural or procedural fix (e.g., constructing a handrail or ramp in lieu of a step) within the problematic areas to limit future incidents within the problematic areas.

In one implementation, the system can track frequencies of incidents throughout various regions of the facility, such as a number of incidents occurring within a region of length proportional to a locational tolerance of the wearable device and hubs per week. For example, in response to a frequency of incidents proximal a location exceeding a threshold frequency during a time window, the system can populate and distribute a work-order to investigate a physical obstacle or structure—near the location—that may be contributing to the increased frequency of local fall events. The system can additionally or alternatively prompt reallocation of resources (i.e., care providers) to monitor this location. In particular, the system can predict presence of a physical obstacle that may be contributing to fall events near a particular location within the facility in response to a frequency of incidents—proximal this location—that exceeds a threshold frequency. The system can compile historical resident location and fall event data into baseline frequencies of fall events incident at various locations (e.g., discrete rooms, five-meter-square grids, etc.) throughout the facility as a function of a number of fall events per total resident-man-hours spent in or near each location. For example, the system can: track locations of all residents of the facility over time as described above; determine that sixty residents walk through a particular hallway per day on average; determine that each resident traverses the hallway over a period of one minute on average; determine that one fall event occurs in the hallway every other day on average; and compile these data into an incident frequency of 0.5 incidents per man-hour in the hallway. Similarly, for a cafeteria, the system can: track locations of all residents of the facility over time as described above; determine that a hundred residents spend an hour in the cafeteria each day on average; determine that, on average, two fall events occur in the cafeteria every day; and compile these data into an incident frequency of 0.02 incidents per man-hour in the cafeteria. In this example, the system can then: prompt an administrator or care provider to send someone to investigate the hallway for torn carpet, misplaced furniture, and/or other tripping hazards; and when a particular resident is moving toward the hallway, prompt a care provider to relocate to the hallway to assist the particular resident in the hallway. Therefore, the system can calculate the hallway is twenty-five times more hazardous than the cafeteria and can thus suggest administrator reallocate resources to the hallway to limit fall events.

Additionally or alternatively, the system can apply similar methods and techniques to quantify fall risk for each location, room, region, grid, etc. within the facility. Therefore, the system can serve suggestions to the care provider and/or administrator portal and selectively prompt care providers to monitor particular rooms with high fall risk based on historical resident location data, historical fall event data, and real-time location of residents.

In another implementation, in response to detecting temporal patterns (e.g., at particular times of day or days of the week) of incidents at a particular location of facility, the system can populate the work-order to deploy a care provider to the particular location to monitor residents in the particular location at times when the incident frequency exceeds a threshold frequency. For example, during a lunch hour, the system can extract a high frequency of fall events in a cafeteria and a low frequency of fall events near an atrium. Thus, the system can populate a work-order to reallocate care providers from the atrium to the cafeteria during the lunch hour to monitor residents within the cafeteria.

8.1 Incident-Triggered Outputs for Community

As shown in FIG. 3, Blocks S240 and S250 of the second method S200 recite, in response to frequency of incidents proximal the first location exceeding a threshold frequency during a time window: populating a work-order to fix topography of an area surrounding the first location and deploy a care provider to the first location during the time window in Block S240; and distributing the work-order to the set of computing devices in Block S250. Generally, the system can automatically populate a work-order, prompt, and/or incident report to address an issue within the facility (e.g., furniture layout) and/or provide assistance to at-risk residents in high-risk locations within the facility.

As described below, the work-order, prompt, and/or incident report can be tailored to stakeholders, such as care providers, other residents, physicians, facility administrators, family, etc. such that the work-order, prompt, and/or incident includes information relevant to the stakeholder and provides details about problems that the stakeholder may remedy.

8.2 Care Provider Prompts

In one implementation, the system can populate a work-order with information relevant to a care provider such as a nurse, a facility administrator, a physician, etc. In response to calculating a frequency of the incidents exceeding a threshold frequency at a particular location or region within the facility, the system can populate a work-order (e.g., fill in fields within a work-order template) with the particular location, quantity of incidents near the particular location (e.g., within five meters), and a list of residents who were involved with past incidents. Furthermore, the work-order can instruct one or more care providers to monitor or assist residents proximal the particular location during time windows when the frequency of incidents at the particular location is highest.

For example, at an assisted-living facility, the system can implement similar techniques as described above to calculate a first frequency of incidents near a step near an atrium of the assisted-living facility between loam and 12 pm; a second frequency of incidents in the cafeteria between loam and 12 pm less than the first frequency of incidents; a third frequency of incidents in the atrium between 12 pm and 2 pm less than the first frequency of incidents and greater than the second frequency of incidents; and a fourth frequency of incidents in the cafeteria between 12 pm and 2 pm greater than third frequency. The system can detect a higher risk for an incident between loam and 12 pm in the atrium than in the cafeteria and a higher risk for an incident between 12 pm and 2 pm in the cafeteria than in the atrium. Thus, the system can generate the work-order including care provider station schedules in which: between loam and 12 pm half of the care providers of the facility are deployed to the atrium, a quarter of the care providers of the facility are deployed to the cafeteria, and the remaining care providers are distributed throughout the rest of the facility; and between 12 pm and 2 pm, a quarter of the care providers of the facility are deployed to the atrium, a third of the care providers of the facility are deployed to the cafeteria, and the remaining care providers are deployed to other areas of the facility. Thus, the system can generate care provider schedules informing where to deploy care providers of the facility to limit incidents throughout the facility.

However, the system can prompt the care provider to assist particular residents and/or the residential community at large in particular locations and during particular time windows in any other suitable way by any other suitable means.

Additionally or alternatively, the system can track the location of care providers similar to the method with which the system can track the location of residents. The system can leverage the current location of care providers to determine which care provider to dispatch in response to a detected event in the facility. Furthermore, the system can calculate the amount of time a care provider spends with each resident at the facility in order to calculate a time dependent insurance reimbursement for the facility.

8.3 Administrator Prompts

In response to detecting a high frequency of incidents at a particular location across all residents (or a subset of residents) of the facility, the system can flag the particular location as a high-risk area and distribute a work-order to a facility administrator highlighting the particular location as a high-risk area in which there may be an architectural or topographical flaw and other obstruction that contributes to the high frequency of incidents at the particular location. Thus, the system can distribute a prompt to a computing device (e.g., mobile phone) affiliated with the administrator to deploy a crew (e.g., a construction crew or care provider) to the particular location to fix or remove the architectural or topographical flaw and other obstruction as shown in FIG. 3.

For example, the system can implement similar techniques as described above to: calculate a frequency of incidents near a sitting-area of a common area in the facility; in response to detecting a high frequency of incidents near the sitting-area, the system can prompt an administrator to investigate a cause for the high frequency of incidents near the sitting-area. The system can also serve incident data and video-surveillance to the computing device to assist the administrator in determining the problem. From the incident data (e.g., time and location), the administrator may determine the coffee table in the sitting-area protrudes into the walkway near the chair and residents frequently trip on a leg of the coffee table. As a result, the work-order can specify removal and replacement of the coffee table as shown in FIG. 3.

Similarly, the system can serve incident reports and incident summaries to computing devices affiliated with facility administrators and/or insurance providers.

However, the system can serve any other work-order, prompt, notification, and/or incident report to a user portal to inform stakeholders of facility flaws and potential fixes for the facility flaws in any other suitable way.

8.4 Community: Resident Prompts

In another implementation, the system can serve a notification of incidents within the facility to a resident portal rendering on a computing device affiliated with a resident, such as a wall-mounted monitor or television within a resident's room. The notification can include locations of incidents proximal the resident and can inform the resident to avoid particular areas of the facility due to high risk of falling and notify the resident that a friend or neighbor has fallen. Generally, the system can serve notifications and prompts to the resident portal to facilitate community within the facility and assist residents in avoiding areas in which they may fall, stumble, require assistance, or may breach their custom access perimeters.

For example, the system can detect that a first resident fell while walking from her room to the cafeteria prior to lunch. The system can thus inform neighbors of the first resident to pay particular attention while ambling toward the cafeteria as there may be an obstacle (e.g., wrinkled carpet or a step) along the path between the cafeteria and the first resident's room. Additionally, the system can render a countdown timer until a crew removes or fixes the obstacle along the path.

9. Resident Activity Tracking

As shown in FIG. 1, the system can track a series of activities detected by a wearable device associated with a user in Blocks S112 and S132. Generally, the wearable devices worn by residents in the facility can include an accelerometer, a gyroscope, a heart rate monitor, and/or other biometric sensors in order to detect various activities of the resident wearing the wearable device. The accelerometer and gyroscope enable the wearable device to perform pattern matching algorithms (e.g., gait analysis/motion tracking algorithms) to detect an activity of the user. In one implementation, each wearable device can detect activities including walking, exercising, sitting (i.e., sitting sedentary behavior), laying (i.e. laying sedentary behavior), and sleeping. Additionally, the wearable device can also detect other activities such as wheeling (a wheel chair), walking with a cane, and/or walking with a walker. Thus, the system can track the first series of activities detected by the first wearable device based on the first series of locations and biometric and motion data recorded at the first wearable device over the first period In one implementation, the facility can assign tracking devices similar to the wearable devices to walkers, canes, wheelchairs, or any other mobility device in order for the system to more accurately detect the activity of the resident. For example, the system can detect that a resident is likely moving using a cane if both the wearable device associated with the resident and the tracker associated with the cane are moving together and at the same time.

In yet another implementation, wearable devices can detect multiple forms of exercise, such as walking, running, stair climbing, elliptical exercise, swimming, cycling, weight lifting, or any other exercise related activity. In this implementation the system can include trackers associated with various exercise equipment, which can indicate whether the exercise equipment is in use, such that the system can detect when residents of the facility are using the exercise equipment (e.g., by detecting that the resident is exhibiting an elevated heartrate in conjunction with the exercise equipment being in use in the same location).

However, the system can detect activities performed by residents of the facility in any other way.

10. Action Profiles

As shown in FIGS. 1 and 2, the system can aggregate a series of locations, a series of activities, and/or a series of incidents detected over a period of time to calculate an action profile for each resident such as in Blocks S120, S122, S140, and S142. Generally, the system can track the location and activity data of the resident in relation to a known floorplan or other map of the facility over time. By analyzing the location and activity data of the resident in relation to the floorplan of the facility, the system can estimate and/or categorize the activity being performed by the resident at any given time. For example, if the resident is located within an area corresponding to the bed of the resident, the system can estimate that the resident is engaging in sedentary behavior and/or sleeping for the time that the resident is in that location. Additionally or alternatively, the system can cross-reference the location data with the activity data to better categorize (e.g., classify) the current action of the resident. For example, the system can detect that a resident is located in an exercise room and detect an activity level for the same time period that indicates sedentary behavior, in this case the system can determine that the resident is not exercising but merely sitting in the exercise room.

In addition to merging the series of locations and the series of activities tracked by the wearable device, the system can also include incident information as part of the action profile. For example, the system can: track a first series of fall events detected by a wearable device over a period of time; calculate a baseline action profile of the resident based on a series of locations, a series of activities, and the first series of fall events; track a second series of fall events over a second period of time; and calculate the second action profile of the resident based on a second series of locations, a second series of activities, and the second series of fall events. Thus, the system can track changes in the frequency, number, and/or severity of fall events of a resident between a baseline action profile and a second action profile.

In one implementation, the system utilizes an action model to transform location and activity data collected from each resident wearable device into an action profile for the resident. The action model can include any type of classifier for identifying each action and the amount of time the resident spends performing each action. In one implementation, the action model is a conditional model that records the resident as performing a particular action when a set of conditions corresponding to that action are satisfied in the location and activities data of the resident. For example, the action model can include a geofence around the toilet of a resident in the facility and classify any time spent within the geofence as a "toileting" activity. Alternatively, the action model can be a supervised learning algorithm that classifies resident behavior based on labels of previously obtained data provided by care providers of residents under care provider supervision.

In one implementation, the system can also calculate secondary action metrics indicating various aspects of the resident's quality of life. For example, the system can include metrics for sleep quality, mobility, sociability, based on observed location and activity data for a resident.

10.1 Individual Actions

The system can identify a number of individual actions of a resident in the facility, such as sleeping, eating, in-room activity, out-of-room activity, toileting, grooming, and/or ambulation. Additionally, the system can identify secondary action metrics including sleep quality, sedentary time, active time, and/or mobility. The system can detect each of these actions via the action model, whereas the system calculates the action metrics based on a combination of actions and/or via a more detailed analysis of location and activity data for a resident within a period already classified as an action.

In one implementation, the system can classify a resident as sleeping when the system detects that the resident is located within a geofence corresponding to the resident's bed and the activity data during the same time is below a motion threshold. Additionally, the system can calculate an action metric estimating the sleep quality of the resident by generating a score that is a function of the average amount of motion observed for the resident while the resident is sleeping and/or the number of times the resident leaves the geofence corresponding to the resident's bed each night between periods of sleep.

In another implementation, the system can classify a resident as eating. For example, if the system detects that a resident is within a geofence corresponding to a cafeteria or another designated eating location within the facility and is performing repetitive motion with her hands then the system can classify the resident as eating for the period of time during which these conditions remain true.

In yet another implementation, the system can classify a resident as performing an "out-of-room" action or an "in-room" action. The system can identify these actions when a resident is inside her room our outside her room but is not performing another particular action.

In another implementation, the system can classify a resident as performing a sedentary when the resident is awake (e.g., indicated via biosignal data or accelerometer data received from the wearable device of the resident) within the same geospatial location. For example, if the system detects consistent accelerometer and gyroscope data from the resident's wearable device greater than a threshold, but the geospatial location of the resident does not change significantly over a period of time, the system can classify that period of time for the resident as "sedentary time." Additionally or alternatively, the system can classify a period of time as "active time" if significant movement is detected as a resident moves from one geospatial location to another. Furthermore, the system can detect an ambulatory motion via accelerometers and gyroscopes in the wearable device, which can improve the ability of the system to detect that the resident is walking from place to place as opposed to being carried or otherwise transferred from place to place.

10.2 Social Actions

As shown in FIG. 2, the system can: track a series of locations of a first wearable device associated with a resident of the facility in Blocks S110 and S130; track a second series of locations of a second device associated with a second user in the facility in Blocks S114 and S134; calculate a first series of proximities of the first wearable device to the second device based on the first series of locations and the second series of locations in Block S160; and calculate an interaction between the resident and the second user based on the first series of proximities in Block S122. In particular, the system can detect actions based on the presence of other residents or care providers (e.g., interactions) in the facility in close proximity to the resident and include those interactions in the action profile.

For example, the system can classify the resident as preforming a social interaction when she is outside of her room and located within a certain proximity of another resident for longer than a threshold period of time. In one implementation, the system can further classify a social interaction based on the location context of the resident during a time in which the two residents are in close proximity. For example, if the resident is in a board game room during the interaction, then the system could classify the resident as playing board games.

Additionally, the system can track interactions between care providers and residents as an action for the resident. For example, the system can identify a "receiving care" action when a care provider is in the room with a resident. Thus, the system can track total amount of care given to each resident in a facility.

As described above with respect to individual actions, the system can detect social interactions (between the resident and other residents or between the resident and care providers) via an action model, which can be a conditional model or a supervised learning model.

In one implementation, in addition to tracking interactions between a resident and another individual in the facility, the system can also include wholistic interactions between a resident and all other residents, all care providers, or all other residents and care providers in the action profile. Thus, an action profile for a resident can include total interaction time, total care provider time, or other summary metrics of a resident's interactions with other individuals in the facility. By detecting interactions on a pairwise basis and on a wholistic level for each resident, the system can differentiate between social changes (e.g., the resident no longer enjoys spending time with a particular friend) and mental health changes (e.g., the resident is depressed and does not spend social time with anyone). In the instance of a social change, the system can prompt a care provider to talk with the resident about the social change. In the instance of a mental health change, the system can prompt a care provider to schedule an appointment for the resident with a psychiatrist or another physician.

10.2.1 Care Provider Interactions

In one implementation, the system can track the location of care providers in the facility, via a smartphone application or a wearable device similar to a resident wearable device, in order to record the amount of time each care provider spends with each patient. For example, the system can detect a period of time a care provider is in the same room as a resident and record that period of time as care providing time. Additionally or alternatively, the system can record time that a care provider spends in close proximity with a resident in a common area of the facility as care providing time. After recording care providing time, the system can tabulate the care providing time and report the care providing time on a care provider and resident basis in order to facilitate insurance reimbursement payments.

Furthermore, the system can identify dependencies or lapses of care between care providers and residents. In one implementation, the system can calculate the amount of time each care provider has spent with each resident and identify outliers. For example, the system can calculate that a single care provider accounts for 60% of the care providing time for a particular resident and can identify this anomaly as a potential risk for dependency between the care provider and the resident; and prompt care providers in the facility to distribute care providing time for the particular resident more evenly across care providers. Alternatively, the system can: calculate that a resident is receiving 50% less total care time than an average resident of the facility; identify this resident as needing additional care time; and prompt care providers in the facility to increase interactions with this resident. Additionally, the system can notify the administrator of the facility in response to identifying an outlier in provider care time. Thus, the system can: in response to the deviation indicating an increase in interactions between the resident and the care provider, the increase in the interactions between the resident and the care provider exceeding the deviation threshold, transmit the prompt to a user associated with the facility to investigate a dependency of the resident on the care provider; and in response to the user identifying the dependency of the resident on the care provider, the system can receive an assignment of a new care provider to the resident.

In one implementation, the system can calculate a baseline level of care provider time for each resident, which can also differentiate the care time based on the type of care given to the resident during that time. Then, in response to observing a change greater than a threshold from the baseline care provider time, the system can notify an administrator of the facility that the change has occurred.

10.2 Baseline Action Profile

As shown in FIG. 1, the system can continuously monitor and classify the actions of each resident in the facility to: calculate a baseline action profile of the resident based on a series of locations and a series of activities during a baseline period of time in Block S120; or calculate a baseline interaction between the resident and a second user based on a series of proximities in Block S122. The system can establish the baseline action profile for a user over multiple periods of time to monitor trends in resident behavior over various time scales. For example, the system can establish a separate baseline action profile for the same resident for the last day, last week, last month, last year, etc.

In generating the baseline action profile for a resident, the system can average each detected action for the resident over the time period (which can be expressed as a time-per-day). For example, if a resident is classified as performing the "sleeping" action for an average of seven hours a day, this can be included in the resident's baseline action profile. In one implementation, the system performs outlier detection to remove periods of time that should not be included in the calculation of a resident's baseline action profile. For example, the system can incorporate calendar data from the facility indicating that a resident visited with family or had a surgical operation on a particular date. The system can then exclude data from the identified periods of time since the daily routine of the resident is likely to have been disrupted during that period of time.

In one implementation, the system can detect cyclical patterns in actions for a resident over weekly or monthly time scales. For example, the system can maintain a separate baseline action profile for each day of the week and/or week of the month in order to account for cyclical scheduling in the facility.

10.4 Revised/Updated Action Profile

As shown in FIG. 1, during a second period of time subsequent to the baseline (first) period of time, the system can calculate an updated action profile (i.e. a revised action profile or a second action profile) of the resident based on the second series of locations and the second series of activities in Block S140. The system can automatically record location data and activity data for a resident and periodically generate an action profile of the resident (e.g., once a day, once a week, etc.). In one implementation, the system can generate multiple action profiles for the most recent day, week, month, etc. and compare those profiles to a baseline action profile of a longer period of time.

Additionally or alternatively, the system can calculate an updated action profile for a second period of time that overlaps with the baseline period of time. For example, the system can calculate a baseline action profile that includes location and activity data of the resident for the last year and a second action profile that includes location and activity data of the resident for the last day.

The system can regularly repeat this process to revise the resident's action profile based on additional activity and location data collected from the resident's wearable device (and/or other devices associated with the resident) over time. For example, the system can calculate: a baseline action profile for the resident over a first period of time; calculate a second action profile for the resident over a second period of time; calculate a third action profile for the resident over a third period of time; etc. The system can then compare these action profiles to the baseline action profile of the resident in order to predict the resident's deviation from her baseline—such as including a magnitude, total time, and/or velocity of this deviation—in a particular activity domain over time.

The system can also merge a resident's recent action profile with the baseline action profile to form a new baseline action profile and compare subsequent action profiles with the updated action profile. For example, the system can: calculate an additional action profile of the resident based on the third series of locations and the third series of activities; merge the second action profile and the baseline action profile to generate a second baseline action profile; and in response to a deviation between the second baseline action profile and the third action profile exceeding the deviation threshold, transmit a prompt to a care provider associated with the facility to prioritize investigating the health status of the resident. Thus, if a first updated action profile deviates from a baseline action profile and a second updated action profile deviates from the second baseline action profile, the system can prioritize the medical care of the resident.

10.5 Detecting Action Profile Deviations

In one implementation, the system can detect whether a deviation between a current action profile of the resident and a baseline action profile of the resident exceeds a deviation threshold; and, in response to the deviation exceeding the deviation threshold, transmit a prompt to a care provider associated with the facility to investigate a health status of the resident in Block S150. Additionally, the system can, in response to a deviation between the baseline interaction and the second interaction exceeding a deviation threshold, transmit a prompt to a third user associated with the facility to investigate a health status of the resident in Block S152.

In one implementation, the system can include preprogrammed thresholds for each type of action or action metric included in the action profiles of the resident. The deviation thresholds can be proportional thresholds (e.g., a reduction or increase of an action of 10%) or absolute magnitude thresholds (e.g., a reduction in sleeping time of one hour). Additionally or alternatively, the system can execute multiple deviation thresholds, which can trigger different outputs depending on the deviation threshold exceeded by an action profile of the resident when compared to a baseline action profile of a resident.

In yet another implementation, the system can calculate a deviation score, which can include a weighted sum of deviations between individual actions in different action profiles. The deviation score can define positive and negative values that represent changes indicating improvement or worsening of the health state of the resident respectively. For example, a positive weighted score of 45 can represent a weighted sum of improvements in sleep quality and exercise time worth 20 and 25 points respectively. Likewise, a score of −35 could indicate a reduction in socialization time and an increase in toileting time.

In another implementation, the system can calculate a baseline action profile for a first time period of location and activity data for a resident; calculate a second action profile for a second time period encompassed by the first time period; detect a deviation between the baseline action profile and the second action profile; and notify a user in the facility that the second time period represents an outlier in the baseline time period. In this manner, the system can identify periods of time within the baseline period of time for which the resident did not exhibit typical behavior and, subsequently, the system can remove those periods of time from the baseline period of time.

Furthermore, the system can calculate a deviation between a second action profile and multiple overlapping baseline action profiles. For example, the system can calculate deviations between a second action profile and a baseline action profile for a last month and a last year, thereby identifying whether the recent behavior captured in the second action profile indicates a change from a recent baseline and long-term baseline action profile. If the system detects a deviation between both baseline action profiles, then the system can notify a care provider of the deviation. If the system, detects a deviation between the second action profile and the longer of the two baseline action profiles, then the system can notify the care provider that the deviation is part of a longer trend that started during the period of the shorter-term baseline period.

10.6 Health Risk Assessment

In one implementation, the system can: calculate a health risk assessment for the resident based on a detected deviation between a second action profile and a baseline action profile; and in response to the health risk assessment exceeding a risk threshold, transmit a prompt to the care provider associated with the facility to schedule a physician appointment for the resident. The system can calculate a health risk assessment based on a supervised model of previous residents at the facility. The health risk assessment model can predict the probability of a physician visit or a particular health outcome (e.g., hospitalization, death, etc.) that would negatively impact the patient. The health risk assessment model takes in an input vector, which can include the baseline action profile of the resident, the second (or any recent) action profile of the resident, and any other electronic health records or demographic data of the resident. Thus, the system can train and implement a supervised learning model capable of generating a health risk assessment of a resident based on deviations between a second action profile and a baseline action profile.

In one implementation, the system can: calculate a mental health risk assessment for the resident based on the deviation; and in response to the mental health risk assessment exceeding a risk threshold, transmit a prompt to a user associated with the facility to schedule a physician appointment for the resident. In this implementation, the system can use only actions involving social interactions and/or other markers of mental health in order to train a mental health risk assessment model. Alternatively, the mental health risk assessment model can utilize the same input vectors but instead predict the likelihood of a particular mental health outcome for the resident.

10.7 Outputs

As shown in FIG. 1, upon detecting a deviation outside of a deviation threshold, the system can send a notification, prompt, and/or work order to a care provider, administrator, and/or any other user of the system who is responsible for a resident. The notification can include information about the deviation, such as the action(s) causing the deviation, the baseline action profile of the resident for which the deviation was detected, and a classification of the deviation as either an improvement or deterioration in the condition of the resident.

In one implementation, if the system has previously identified a deviation upon comparing the baseline action profile of the resident to a previous action profile, the system can issue a warning to the user of the system that the action profile of the resident continues to deviate from the baseline action profile of the resident. Furthermore, the system can prioritize a previously transmitted prompt in response to a resident's continued deviation from their baseline action profile over multiple days, weeks, months, etc. For example, the system can: over a third period, track a third series of locations of the first wearable device; and track a third series of activities detected by the first wearable device; calculate a third action profile of the resident based on the third series of locations and the third series of activities; and, in response to a deviation between the baseline action profile and the third action profile exceeding the deviation threshold, transmit a prompt to a care provider associated with the facility to prioritize investigating the health status of the resident.

In addition to transmitting prompts to care providers and other users, the system can generate a work order for a care provider to schedule a physician appointment for a resident in response to detecting a deviation between an updated action profile of the resident and a baseline action profile of the resident. In this implementation, the system can provide an interface to the care provider to complete the work order and schedule a physician appointment for the resident via the native care provider application.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for assessing health status of residents of a facility, comprising:
over a first period:
tracking a first series of locations of a first wearable device associated with a resident of the facility; and
tracking a second series of locations of a second device associated with a second user in the facility;
calculating a first series of proximities of the first wearable device to the second device over the first period based on the first series of locations and the second series of locations;
calculating a baseline interaction between the resident and the second user based on the first series of proximities;
over a second period:
tracking a third series of locations of the first wearable device; and
tracking a fourth series of locations of the second device;
calculating a second series of proximities of the first wearable device to the second device over the second period based on the third series of locations and the fourth series of locations;
calculating a second interaction between the resident and the second user based on the second series of proximities; and
in response to a deviation between the baseline interaction and the second interaction exceeding a deviation threshold, transmitting a prompt to a third user associated with the facility to investigate a health status of the resident.

2. The method of claim 1, wherein:
tracking the second series of locations of the second device associated with the second user in the facility over the first period further comprises tracking the second series of locations of the second device associated with a second resident of the facility;
calculating the baseline interaction between the resident and the second user based on the first series of proximities further comprises calculating the baseline interaction between the resident and the second resident based on the first series of proximities; and
calculating the second interaction between the resident and the second user based on the proximity of the first wearable device to the second device over the second period further comprises calculating the second interaction between the resident and the second resident based on the proximity of the first wearable device to the second device over the second period.

3. The method of claim 1, wherein:
tracking the second series of locations of the second device associated with the second user in the facility over the first period further comprises tracking the second series of locations of the second device associated with a care provider associated with the facility;
calculating the baseline interaction between the resident and the second user based on the first series of proximities further comprises calculating the baseline interaction between the resident and the care provider based on the first series of proximities; and
calculating the second interaction between the resident and the second user based on the proximity of the first wearable device to the second device over the second period further comprises calculating the second interaction between the resident and the care provider based on the proximity of the first wearable device to the second device over the second period.

4. The method of claim 3, wherein, in response to the deviation between the baseline interaction and the second interaction exceeding the deviation threshold, transmitting the prompt to the third user associated with the facility to investigate the health status of the resident further comprises:
in response to the deviation indicating an increase in interactions between the resident and the care provider, the increase in the interactions between the resident and the care provider exceeding the deviation threshold, transmitting the prompt to the third user associated with the facility to investigate a dependency of the resident on the care provider; and
in response to the third user identifying the dependency of the resident on the care provider, receiving an assignment of a new care provider to the resident.

5. The method of claim 1:
wherein tracking the second series of locations of the second device associated with the second user in the facility over the first period further comprises tracking the second series of locations of the second device associated with a first care provider associated with the facility;
further comprising:
over the first period, tracking a fifth series of locations of a third device associated with a second care provider in the facility; and calculating a third series of proximities of the first wearable device to the third device over the first period based on the first series of locations and the fifth series of locations;

wherein calculating the baseline interaction between the resident and the second user based on the first series of proximities further comprises calculating a baseline total care between the resident and the first care provider and between the resident and the second care provider based on the first series of proximities and the third series of proximities;

further comprising:
over the second period, tracking a sixth series of locations of the third device; and
calculating a fourth series of proximities of the first wearable device to the third device over the second period based on the third series of locations and the sixth series of locations;

wherein calculating the second interaction between the resident and the second user based on the second series of proximities further comprises calculating a second total care between the resident and the first care provider and between the resident and the second care provider based on the second series of proximities and the fourth series of proximities;

wherein transmitting the prompt to the third user associated with the facility to investigate the health status of the resident further comprises, in response to a deviation between the baseline total care and the second total care exceeding the deviation threshold, transmitting a prompt to the third user associated with the facility to investigate a lapse in care for the resident; and further comprising, in response to identifying the lapse in care for the resident, generating a work order to increase care for the resident.

6. The method of claim 1:
further comprising:
over the first period, tracking a fifth series of locations of a third device associated with a fourth user in the facility; and
calculating a third series of proximities of the first wearable device to the third device over the first period based on the first series of locations and the fifth series of locations;

wherein calculating the baseline interaction between the resident and the second user based on the first series of proximities further comprises calculating a baseline total interaction between the resident and the second user and between the resident and the fourth user based on the first series of proximities and the third series of proximities;

further comprising:
over the second period, tracking a sixth series of locations of the third device; and
calculating a fourth series of proximities of the first wearable device to the third device over the second period based on the third series of locations and the sixth series of locations;

wherein calculating the second interaction between the resident and the second user based on the second series of proximities further comprises calculating a second total interaction between the resident and the second user and between the resident and the fourth user based on the second series of proximities and the fourth series of proximities; and wherein transmitting the prompt to the third user associated with the facility to investigate the health status of the resident further comprises, in response to a deviation between the baseline total interaction and the second total interaction exceeding the deviation threshold, transmitting a prompt to the third user associated with the facility to investigate the health status of the resident.

7. The method of claim 1, further comprising:
calculating a mental health risk assessment for the resident based on the deviation; and
In response to the mental health risk assessment exceeding a risk threshold, transmitting a prompt to the third user associated with the facility to schedule a physician appointment for the resident.

8. A method for assessing health risk of a resident at a facility, comprising:
over a first period:
tracking a first series of locations of a first wearable device associated with a resident of the facility; and
tracking a first series of activities detected by the first wearable device;
calculating a baseline action profile of the resident based on the first series of locations and the first series of activities, wherein the baseline action profile includes a location-based action of the resident;
over a second period:
tracking a second series of locations of the first wearable device; and
tracking a second series of activities detected by the first wearable device;
calculating a second action profile of the resident based on the second series of locations and the second series of activities, wherein the second action profile includes a location-based action of the resident; and
in response to a deviation between the baseline action profile and the second action profile exceeding a deviation threshold, transmitting a prompt to a care provider associated with the facility to investigate a health status of the resident and assigning an additional care provider to the resident.

9. The method of claim 8:
further comprising:
over the first period, tracking a third series of locations of a second device associated with a second user in the facility; and
calculating a first series of proximities of the first wearable device to the second device over the first period based on the first series of locations and the third series of locations;

wherein calculating the baseline action profile of the resident based on the first series of locations and the first series of activities further comprises calculating the baseline action profile of the resident based on the first series of locations, the first series of activities, and the first series of proximities;

further comprising:
over the second period, tracking a fourth series of locations of the second device; and
calculating a second series of proximities of the first wearable device and the second device based on the second series of locations and the fourth series of locations; and wherein calculating the second action profile of the resident based on the second series of locations and the second series of activities further comprises calculating the second action profile of the resident based on the second series of locations, the second series of activities, and the second series of proximities.

10. The method of claim 9, wherein
calculating the baseline action profile of the resident based on the first series of locations, the first series of activities, and the first series of proximities further comprises calculating the baseline action profile comprising at least one of:
  a baseline interaction time between the resident and the second user based on the first series of proximities;
  a baseline interaction frequency between the resident and the second user based on the first series of proximities; and
  a baseline interaction score of interactions between the resident and the second user based on the first series of proximities and the first series of locations; and
calculating the second action profile of the resident based on the second series of locations, the second series of activities, and the second series of proximities further comprises calculating the second action profile comprising at least one of:
  a second interaction time between the resident and the second user based on the second series of proximities;
  a second interaction frequency between the resident and the second user based on the second series of proximities; and
  a second interaction score of interactions between the resident and the second user based on the first series of proximities and the first series of locations.

11. The method of claim 8:
further comprising:
  accessing a floorplan of the facility; and
  accessing a geofence in the floorplan associated with the resident and corresponding to the location-based action of the resident; and
wherein:
  calculating the baseline action profile of the resident based on the first series of locations and the first series of activities further comprises, in response to a first subset of locations in the first series of locations situated within the geofence, calculating the baseline action profile of the resident comprising the location-based action based on the first subset of locations; and
  calculating the second action profile of the resident based on the second series of locations and the second series of activities further comprises, in response to a second subset of locations in the second series of locations situated within the geofence, calculating the second action profile of the resident comprising the location-based action based on the second subset of locations.

12. The method of claim 8:
further comprising, over the first period, tracking a first series of fall events detected by the first wearable device;
wherein calculating the baseline action profile of the resident based on the first series of locations and the first series of activities further comprises calculating the baseline action profile of the resident based on the first series of locations, the first series of activities, and the first series of fall events;
further comprising, over the second period, tracking a second series of fall events detected by the first wearable device; and
wherein calculating the second action profile of the resident based on the second series of locations and the second series of activities further comprises calculating the second action profile of the resident based on the second series of locations, the second series of activities, and the second series of fall events.

13. The method of claim 8, wherein:
tracking the first series of activities detected by the first wearable device further comprises tracking the first series of activities detected by the first wearable device based on the first series of locations and biometric and motion data recorded at the first wearable device over the first period; and
tracking the second series of activities detected by the first wearable device further comprises tracking the second series of activities detected by the first wearable device based on the second series of locations and biometric and motion data recorded at the first wearable device over the second period.

14. The method of claim 13, wherein:
tracking the first series of activities detected by the first wearable device based on the first series of locations and biometric and motion data recorded at the first wearable device over the first period further comprises tracking the first series of activities detected by the first wearable device based on the first series of locations and biometric and motion data recorded at the first wearable device over the first period, the first series of activities including at least one of: walking; sleeping; exercising; and sedentary sitting; and
tracking the second series of activities detected by the first wearable device based on the second series of locations and biometric and motion data recorded at the first wearable device over the second period further comprises tracking the second series of activities detected by the first wearable device based on the second series of locations and biometric and motion data recorded at the first wearable device over the second period, the second series of activities including at least one of: walking; sleeping; exercising; and sedentary sitting.

15. The method of claim 8, further comprising:
calculating a health risk assessment for the resident based on the deviation; and
in response to the health risk assessment exceeding a risk threshold, transmitting a prompt to the care provider associated with the facility to schedule a physician appointment for the resident.

16. The method of claim 8:
further comprising, over a third period comprising the first period:
  tracking a third series of locations of the first wearable device; and
  tracking a third series of activities detected by the first wearable device;
further comprising calculating a second baseline action profile of the resident based on the third series of locations and the third series of activities; and
wherein, transmitting the prompt to the care provider associated with the facility to investigate the health status of the resident further comprises, in response to the deviation between the baseline action profile and the second action profile exceeding the deviation threshold and a deviation between the second baseline action profile and the second action profile exceeding the deviation threshold, transmitting a prompt to the care provider associated with the facility to schedule a physician appointment for the resident.

17. The method of claim 8, further comprising:
over a third period:

tracking a third series of locations of the first wearable device; and
tracking a third series of activities detected by the first wearable device;
calculating a third action profile of the resident based on the third series of locations and the third series of activities; and
in response to a deviation between the baseline action profile and the third action profile exceeding the deviation threshold, transmitting a prompt to a care provider associated with the facility to prioritize investigating the health status of the resident.

18. The method of claim 8, further comprising:
over a third period:
tracking a third series of locations of the first wearable device; and
tracking a third series of activities detected by the first wearable device;
calculating a third action profile of the resident based on the third series of locations and the third series of activities;
merging the second action profile and the baseline action profile to generate a second baseline action profile; and
in response to a deviation between the second baseline action profile and the third action profile exceeding the deviation threshold, transmitting a prompt to a care provider associated with the facility to prioritize investigating the health status of the resident.

19. The method of claim 8, further comprising:
over a third period:
tracking a third series of locations of the first wearable device; and
tracking a third series of activities detected by the first wearable device;
calculating a third action profile of the resident based on the third series of locations and the third series of activities; and
in response to a deviation between the baseline action profile and the third action profile exceeding a second deviation threshold greater than the deviation threshold, transmitting a prompt to a care provider associated with the facility to prioritize investigating the health status of the resident.

20. A method for assessing health risk of a resident at a facility, comprising:
accessing a floorplan of the facility;
accessing a geofence in the floorplan associated with the resident;
over a first period:
tracking a first series of locations of a first wearable device associated with a resident of the facility; and
tracking a first series of activities detected by the first wearable device;
calculating a baseline action profile of the resident based on the first series of locations and the first series of activities, wherein the baseline action profile includes a location-based action of the resident, wherein the geofence corresponds to the location-based action of the resident, and wherein in response to a first subset of locations in the first series of locations situated within the geofence, calculating the baseline action profile of the resident comprising the location-based action based on the first subset of locations;
over a second period:
tracking a second series of locations of the first wearable device; and
tracking a second series of activities detected by the first wearable device;
calculating a second action profile of the resident based on the second series of locations and the second series of activities, wherein the second action profile includes a location-based action of the resident, wherein in response to a second subset of locations in the second series of locations situated within the geofence, calculating the second action profile of the resident comprising the location-based action based on the second subset of locations; and
in response to a deviation between the baseline action profile and the second action profile exceeding a deviation threshold, transmitting a prompt to a care provider associated with the facility to investigate a health status of the resident.

* * * * *